United States Patent [19]

Nakatsuka et al.

[11] Patent Number: 4,687,852
[45] Date of Patent: Aug. 18, 1987

[54] RADIOACTIVE IODOSPIROPERIDOL

[75] Inventors: Iwao Nakatsuka, Kobe; Hiroshi Shimizu, Takarazuka; Akira Yoshitake, Kyoto, all of Japan

[73] Assignee: Sumitomo Chemical Company, Limited, Osaka, Japan

[21] Appl. No.: 794,860
[22] PCT Filed: May 22, 1984
[86] PCT No.: PCT/JP84/00257
§ 371 Date: Oct. 15, 1985
§ 102(e) Date: Oct. 15, 1985
[87] PCT Pub. No.: WO85/05359
PCT Pub. Date: Dec. 5, 1985

[51] Int. Cl.⁴ .......................................... C07D 471/10
[52] U.S. Cl. .................................................... 546/20
[58] Field of Search ......................................... 546/20

[56] References Cited

U.S. PATENT DOCUMENTS 3,238,216  3/1966  Janssen .................................. 546/20

Primary Examiner—Robert T. Bond
Attorney, Agent, or Firm—Stevens, Davis, Miller & Mosher

[57] ABSTRACT

A radioactive 2-iodospiroperidol represented by the formula:

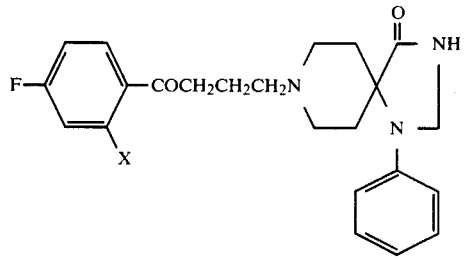

wherein X represents a radioactive iodine atom. This compound has a strong affinity for dopamine receptor and is very useful as a nuclear medical diagnostic agent of dopamine receptor and as a radioactive medicine.

4 Claims, No Drawings

RADIOACTIVE IODOSPIROPERIDOL

TECHNICAL FIELD

This invention relates to a novel radioactive 2iodospiroperidol and a process for preparing the same.

The compound of this invention is a novel compound not disclosed in any literature. This compound has a strong affinity for dopamine receptor and is very useful as a nuclear medical diagnostic agent of dopamine receptor and as a radioactive medicine.

BACKGROUND ART

It has recently been found that in the pathological state of brain (such as Parkinson's disease or schizophrenia), the amount of dopamine receptor is different from that in the normal person, and attention has become directed to the relation between dopamine receptor and various kinds of brain diseases in the fields of medicine and pharmacology. Under these circumstances, the advent of a nuclear medical diagnostic agent and a radioactive medicine targeting dopamine receptor has been strongly desired.

DISCLOSURE OF INVENTION

The present inventors have made extensive studies aiming at obtaining a dopamine receptor-tropic diagnostic agent and a radioactive medicine having radioactive iodine in its molecule, and have found that the novel iodine compound represented by the formula (I) shown below has a strong affinity for dopamine receptor and can be specifically combined therewith.

According to this invention, there is provided a novel radioactive 2-iodospiroperidol represented by the formula (I):

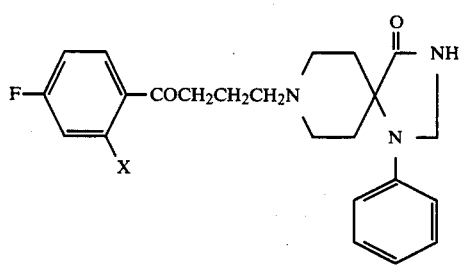

wherein X represents a radioactive iodine atom, and a process for preparing the same. The compound (I) of this invention has a much stronger affinity for dopamine receptor than p-iodospiroperidol which is a known iodine compound disclosed in literature [J. Nuclear Medicine, 23(5), 100 (1982)], and possesses very excellent properties as a dopamine receptor-tropic radioactive diagnostic agent or radioactive medicine.

Therefore, proper application of the compound (I) of this invention makes it possible not only to non-invasively detect the presence of dopamine receptor in the brain and other internal organs and tissues of human beings and animals but also to dynamically measure the change of amount of the receptor, and thus, this compound is greatly useful for the nuclear medical diagnosis and treatment of brain troubles and other diseases. Also, in view of the relevancy of dopamine receptor to cancers such as breast cancer and the like, the compound is also useful in application to this field.

BEST MODE FOR CARRYING OUT THE INVENTION

The method for the preparation of the compound of this invention will be described below.

The compound of this invention represented by the above-mentioned formula (I) can be produced by a conventional method for the synthesis of radioactive iodine compounds. For instance, it can be produced according to either Process A or Process B shown below.

[Process A]

An amino compound represented by the formula (II):

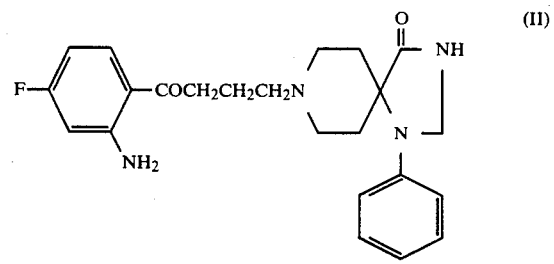

is reacted with an alkali metal salt of nitrous acid in a suitable solvent such as tetrahydrofuran, dioxane, acetonitrile or the like in the presence of an acid such as diluted sulfuric acid or diluted hydrochloric acid to form a diazonium salt represented by the formula (III):

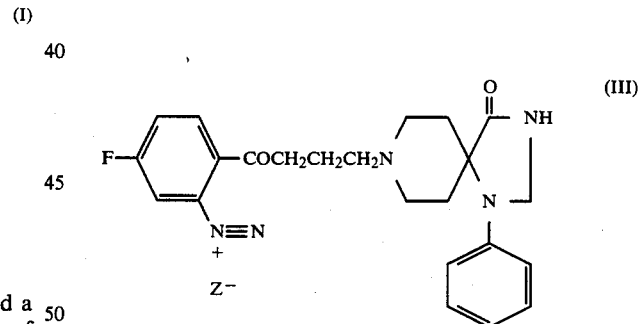

wherein $Z^-$ represents an anion represented by a halogen ion or the formula $HSO_4^-$.

Then the compound (III) is reacted with a radioactive iodine metal salt to obtain the compound of the formula (I). The above reactions are carried out at a temperature in a range of $-5°$ to $30°$ C.

The compound (I) obtained can be purified by a conventional method such as thin layer chromatography (TLC) or high-performance liquid chromatography (HPLC).

[Process B]

A halogeno compound represented by the formula (IV):

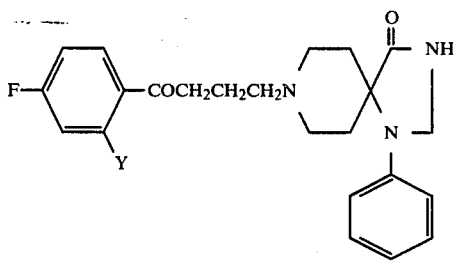

wherein Y represents a halogen atom is subjected to an exchange reaction with a radioactive iodine metal salt in a suitable solvent such as acetonitrile, dimethylformamide, ethylene glycol, an ether derivative of ethylene glycol, an ether derivative of diethylene glycol, water or the like at a temperature of 50° to 180° C. The compound (I) obtained can be purified by a conventional method such as TLC or HPLC.

In the process of this invention, for example, I-123, I-125, I-131, I-132, etc. are exemplified as the radioactive iodine atom, and I-123, I-125 and I-131 are preferred. The radioactive iodine metal salt means a metal salt of the above radioactive iodine, and may be any of those capable of providing a radioactive $I^-$ ion, though alkali metal salts such as, for example, sodium iodide, potassium iodide and lithium iodide are preferred. As the halogen ion in the formula (III), anions of chlorine, bromine, iodine and the like are exemplified, and as the halogen atom in the formula (IV), there can be exemplified, for example, fluorine, chlorine, bromine and iodine atoms.

By intravenously injecting the radioactive 2-iodospiroperidol (I) obtained by this invention into patients and taking a scintigram with the lapse of time, or by measuring the radioactivity by the probe method and determining the intake of the compound (I) in a specific organ, it is possible to simply and appropriately determine the site and scope of the focus and the degree of affection.

The radioactive 2-iodospiroperidol according to this invention is thus useful for the diagnosis of the brain diseases, breast cancer and the like, but this compound is also useful for the diagnosis and treatment of other various diseases resulting from a change of dopamine receptor.

The present invention will further be specifically described below referring to Examples.

REFERENTIAL EXAMPLE

Preparation of 8-[4-(4-fluoro-2-iodophenyl)-4-oxobutyl]-1-phenyl-1,3,8-triazaspiro[4,5]decane-4-one(2-iodospiroperidol)

2-Aminospiroperidol (410 mg) was suspended in 2 N hydrochloric acid and acetonitrile, and to the resulting suspension was added dropwise an aqueous solution of sodium nitrite (95 mg) with ice-cooling. The resulting mixture was stirred at a temperature of 5° C. or less for 30 minutes and an aqueous solution of potassium iodide (166 mg) was added dropwise to the diazonium salt produced with ice-cooling, after which the mixture obtained was further stirred at the same temperature for 1.5 hours. After the reaction, the reaction mixture was made alkaline and subjected to a solvent extraction, and the solvent was then removed by distillation to obtain a crude product. This was purified by silica gel column chromatography to obtain 2-iodospiroperidol (427 mg).

Melting point: 170°–175° C.

IR (CHCl$_3$) cm$^{-1}$: 1710 (C=O).

$^1$H–NMR (CDCl$_3$) δ(ppm): 1.40–3.18 (14H, m, methylene), 4.72 (2H, s, —NHCH$_2$N<), 6.31–7.79 (8H, m, benzene ring H).

Mass spectrum (70 eV) m/e: 521 [M+], 244.

EXAMPLE 1

Preparation of [$^{125}$I]-8-[4-(4-fluoro-2-iodophenyl)-4-oxobutyl]-1-phenyl-1,3,8-triazaspiro[4,5]decane-4-one([$^{125}$I]-2-iodospiroperidol)

The diazonium salt prepared by using 2-aminospiroperidol (40 μg), 2 N sulfuric acid and sodium nitrite was reacted with Na $^{125}$I (2 mCi) with ice-cooling in the same way as in the Referential Example, and the resulting crude product was purified by HPLC (column: Licrosorb ® RP-18) to obtain [$^{125}$I]-2-iodospiroperidol (1.4 mCi). This product was identical with the specimen obtained in the Referential Example in Rf values of TLC and retention time of HPLC.

EXAMPLE 2

Preparation of [$^{123}$I]-2-iodospiroperidol with Na$^{123}$I

In the same manner as in Example 1 using Na$^{123}$I (5 mCi), there was obtained [$^{123}$I]-2-iodospiroperidol (1.4 mCi). This product was identical with the specimen obtained in the Referential Example in Rf values of TLC and retention time of HPLC.

EXAMPLE 3

Preparation of [$^{125}$I]-2-iodospiroperidol by exchange method

Dimethylformamide (10 μl) and Na$^{125}$I (2.2 mCi) were added to 2-iodospiroperidol (3 μg) synthesized by the method of the Referential Example, and a slight amount of 0.1 N sulfuric acid was further added thereto, and the resulting mixture was heated. After the reaction, the resulting crude product was purified by HPLC to obtain [$^{125}$I]-2-iodospiroperidol (0.9 mCi). This product was identical with the specimen obtained in the Referential Example in Rf values of TLC and retention time of HPLC.

We claim:

1. A radioactive 2-iodospiroperidol represented by the formula:

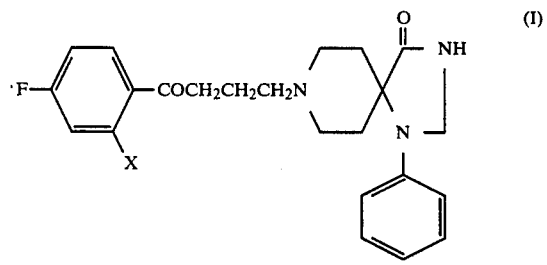

wherein X is a radioactive iodine atom.

2. A radioactive 2-iodospiroperidol according to claim 1, wherein X is an atom selected from the group of radioactive iodine isotopes consisting of I-123, I-125, I-131 and I-132.

3. A radioactive 2-iodospiroperidol according to claim 2, wherein X is I-123, I-125 or I-131.

4. A 2-iodospiroperidol represented by the formula:

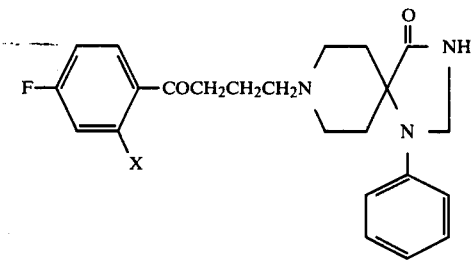
wherein X is an iodine atom.
\* \* \* \* \*
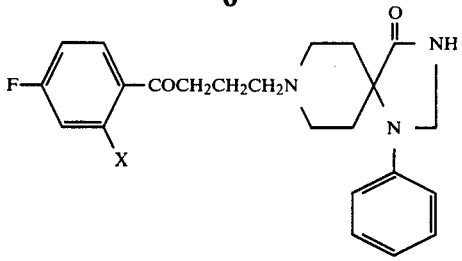
wherein X is an iodine atom.
\* \* \* \* \*